United States Patent [19]

Noiles

[11] 4,198,971
[45] Apr. 22, 1980

[54] DRIP CHAMBER WITH AIR VENT

[75] Inventor: Douglas G. Noiles, New Canaan, Conn.

[73] Assignee: United States Surgical Corporation, Stamford, Conn.

[21] Appl. No.: 865,971

[22] Filed: Dec. 30, 1977

Related U.S. Application Data

[63] Continuation of Ser. No. 579,584, May 21, 1975, abandoned.

[51] Int. Cl.² ............................................. A61M 5/16
[52] U.S. Cl. .............................. 128/214 C; 73/194 R; 128/214.2; 128/214 R
[58] Field of Search ............ 128/214 C, 214 R, 214.2, 128/203, 166, 227; 73/194 R

[56] References Cited

U.S. PATENT DOCUMENTS

| | | | |
|---|---|---|---|
| 3,316,908 | 5/1967 | Burke | 128/214 C |
| 3,659,629 | 5/1972 | Deaton | 128/214 C |
| 3,967,620 | 7/1976 | Noiles | 128/214 C |
| 3,982,534 | 9/1976 | Buckman | 128/214 C |
| 4,056,100 | 11/1977 | Noiles | 128/214 C |

FOREIGN PATENT DOCUMENTS

| | | | |
|---|---|---|---|
| 2161828 | 6/1972 | Fed. Rep. of Germany | 128/214 C |
| 817387 | 7/1959 | United Kingdom | 128/214 C |
| 1182016 | 2/1970 | United Kingdom | 128/214 C |

*Primary Examiner*—William R. Browne
*Attorney, Agent, or Firm*—Fleit & Jacobson

[57] ABSTRACT

An intravenous set with a volume limiting chamber for precisely controlling the volume of parenteral solution administered to a patient and a drip chamber for determining the parenteral solution flow rate. The volume limiting chamber has a membrane valve which when wet will pass parenteral solution but will not pass air at normal intravenous administration pressures. The drip chamber has an air vent so that air can be vented to the drip chamber to lower the liquid level whenever the level is so high that the flow rate cannot easily be determined. The air vent can also be used to vent air from the drip chamber as an aid in priming the drip chamber.

11 Claims, 7 Drawing Figures

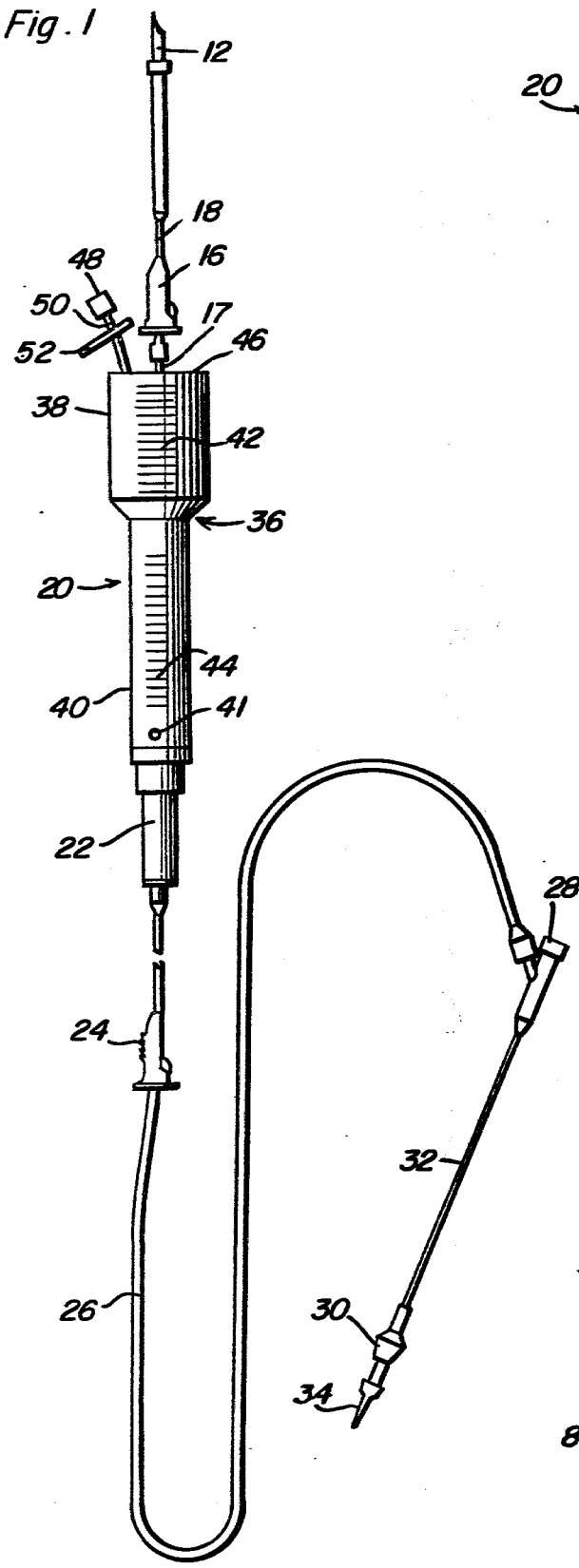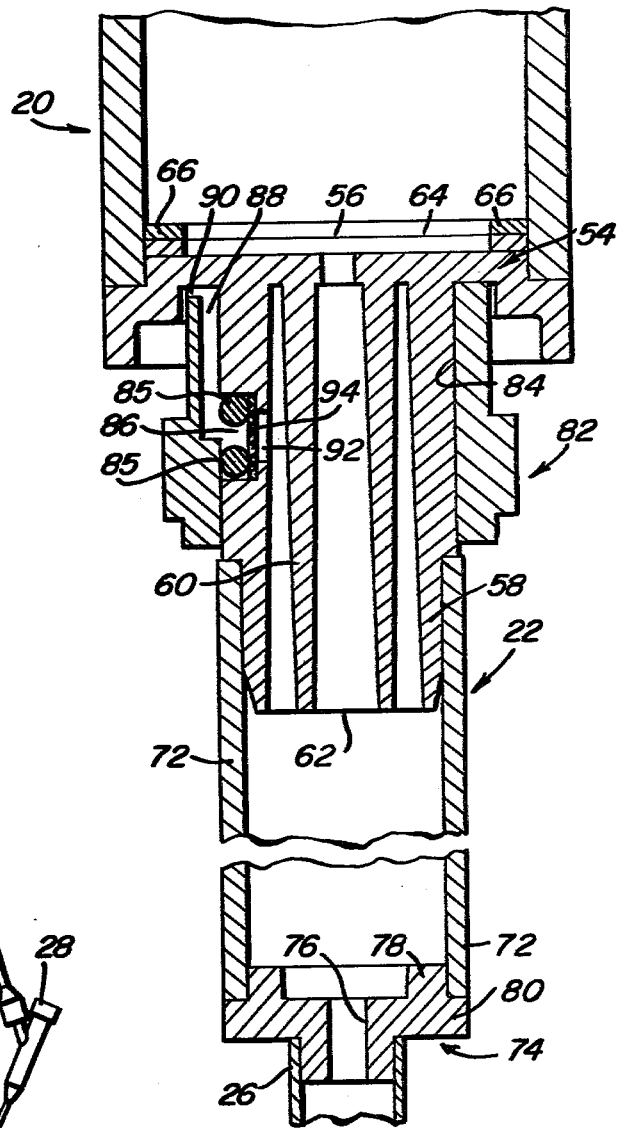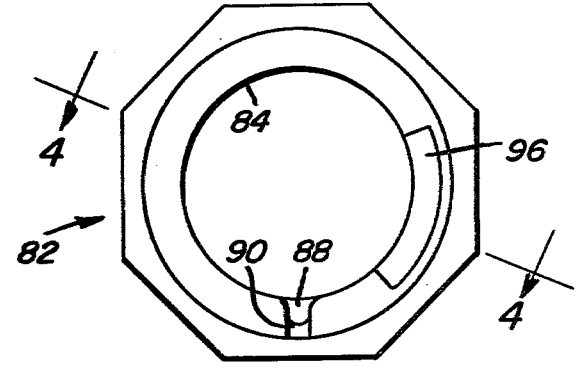

DRIP CHAMBER WITH AIR VENT

This is a continuation of application Ser. No. 579,584, filed May 21, 1975, now abandoned.

BACKGROUND OF THE INVENTION

This invention relates to an improved drip chamber for use in an intravenous set.

Intravenous sets for the administration of parenteral solution to a patient typically include a piercer for insertion into a parenteral solution container, flexible tubing for transporting the parenteral solution from the container to the patient, a lower flow control clamp which acts on the flexible tubing to control the flow rate of the parenteral solution, and a needle adapter to which an intravenous needle is attached. The flow rate is determined by a flow meter such as a drip chamber positioned upstream of the lower clamp.

The intravenous set may also include a volume limiting chamber positioned between the piercer and the flow meter and an upper flow control clamp positioned upstream of the volume limiting chamber. The volume limiting chamber is used to precisely control the volume of parenteral solution administered to the patient. The volume limiting chamber is commonly designed to automatically shut off after a measured volume of parenteral solution is fed to the patient. This is accomplished in many intravenous sets by a membrane valve mounted in the bottom of the volume limiting chamber. Basically, the membrane valve comprises a material which when wet will pass parenteral solution but will not pass air at normal intravenous administration pressures.

A parenteral solution passage is provided in the volume limiting chamber for transferring parenteral solution from the chamber, typically directly into a flow meter. When a drip chamber is used as the flow meter, the discharge opening of the parenteral solution passage in the volume limiting chamber comprises a drop-forming orifice for forming drops of predetermined size. The drops emerge from the drop-forming orifice and fall through the drip chamber where they are counted per unit time and the flow rate of the parenteral solution thereby determined. Smaller size drops are preferred in certain applications, particularly for intravenous sets used in pediatric applications, and so the drop-forming orifice of the volume limiting chamber is frequently adapted to accept a plastic plug containing a very small diameter metal tube or cannula which will form small size drops, commonly sixty drops per cubic centimeter. In any event, it is obvious that the drip chamber will not function properly unless sufficient air space is provided below the drop-forming orifice for the rate of drop formation to be observed.

In using an intravenous set of this type, both the upper and lower control clamps are closed and the piercer is inserted into the outlet of a parenteral solution container. The upper flow control clamp is then opened and the volume limiting chamber partially filled with parenteral solution. After the upper flow control clamp is again closed, the set must be primed. This is accomplished by opening the lower flow control clamp, squeezing the drip chamber and then closing the lower flow control clamp. The drip chamber is then released and will partially fill with parenteral solution. This priming step is repeated until the drip chamber is approximately half filled. The lower flow control clamp must be opened during the priming operation so that the membrane valve will not be damaged. This priming operation is tedious and time consuming and runs the risk of damaging the delicate membrane valve unless strictly followed.

Furthermore, it sometimes happens that the nurse or other attendant will prime the drip chamber to such a high liquid level that insufficient air space remains for the drop rate to be determined. The liquid level can also become too high even when the drip chamber is properly primed. Parenteral solutions are commonly vacuum packed. As a result of this, the parenteral solution is capable of absorbing air from the air space in the drip chamber. This absorbtion of air causes a decrease in the volume of air in the drip chamber and a consequent increase in the volume of parenteral solution in the drip chamber which raises the liquid level. Since the membrane valve in the volume limiting chamber will not pass air when wet, there is no convenient way of admitting air into the drip chamber to lower the liquid level once the level has risen too high. Consequently, the expensive intravenous set is rendered useless because the flow rate therethrough cannot be determined.

Accordingly, an object of this invention is to provide an improved drip chamber.

A further object of this invention is to provide an improved drip chamber having an air vent.

Yet a further object of this invention is to provide an air vent in a drip chamber which includes an air filter.

Another object of this invention is to provide an improved drip chamber in which air can be vented to or from the drip chamber when it is desired to change the liquid level in the drip chamber.

Yet another object of this invention is to provide an improved intravenous set having a volume limiting chamber with a membrane valve and a drip chamber in which air can be vented to or from the drip chamber when it is necessary to adjust the liquid level in the drip chamber.

A still further object of this invention is to provide an improved drip chamber in which the liquid level can be lowered without damaging the delicate membrane valve in the volume limiting chamber.

Yet another object of this invention is to provide an air vent in a drip chamber to facilitate priming the drip chamber.

SUMMARY OF THE INVENTION

A drip chamber is provided in accordance with this invention for use in an intravenous set having a volume limiting chamber with a membrane valve. The membrane valve is used for automatically shutting off the intravenous set after a measured volume of parenteral solution is fed to the patient. The membrane valve when wet will not pass air under normal intravenous administration pressures. Accordingly, in prior art sets the liquid level in the drip chamber cannot easily be changed after the drip chamber is primed because the membrane valve is wet. This difficulty is overcome by providing a normally closed air vent in the drip chamber which allows air to enter or leave the drip chamber when it is desired to change the liquid level. The air vent can also be used to facilitate priming the drip chamber.

BRIEF DESCRIPTION OF THE DRAWINGS

FIG. 1 is a schematic view of an intravenous set having the drip chamber of this invention incorporated therein;

FIG. 2 is an enlarged cross-sectional view of one embodiment of the drip chamber of this invention;

FIG. 3 is a top view of the vent cap of the embodiment of the drip chamber shown in FIG. 2;

DESCRIPTION OF THE PREFERRED EMBODIMENTS

Figure 4:
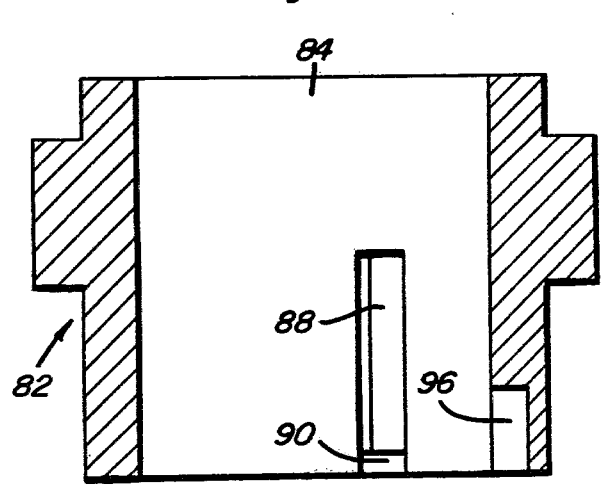
FIG. 4 is a vertical cross-sectional view of the vent cap of FIG. 3 taken along the lines 4—4.

Referring now to FIG. 1, the drip chamber of this invention is shown in an intravenous set for administering parenteral solution to a patient. The intravenous set includes piercer 12 for attaching the intravenous set to the outlet of a parenteral solution container (not shown). Transfer of parenteral solution from the parenteral solution container to volume limiting chamber 20 is controlled by first or upper compression clamp 16 which acts on flexible plastic tubing 18, typically formed from polyvinyl chloride. Drip chamber 22 of this invention is connected to the bottom of volume limiting chamber 20 and is used to determine the flow rate of parenteral solution issuing from volume limiting chamber 20. This flow rate can be controlled by second or lower compression clamp 24 which acts on flexible plastic tubing 26. Tubing 26, also typically formed from polyvinyl chloride, connects drip chamber 22 to Y-injection site 28. Y-injection site 28 can be used for injecting additional medication into the parenteral fluid flow line downstream from volume limiting chamber 20. Y-injection site 28 is connected to injection bulb 30 by flexible plastic tubing 32 which is similar to tubings 18 and 26. Finally, the intravenous set includes needle adapter 34 for attaching an intravenous needle to the set.

Still referring to FIG. 1, volume limiting chamber 20, typically made from a styrene-acrylonitrile polymer, comprises side walls 36 having upper portion 38 and lower portion 40. Upper portion 38 is generally oval in cross-section and has a larger cross-sectional area than lower portion 40 which is generally circular in cross-section. Upper portion 38 has a first set of indicia 42 associated therewith and low portion 40 has a second set of indicia 44 associated therewith for determining the volume of parenteral fluid in the volume limiting chamber. Upper portion 38 of the volume limiting chamber is closed by upper end cap 46 which defines an inlet conduit (17) connected to flexible plastic tubing 18. Air vent 48 is connected to chamber 20 by flexible tubing 50. Slide clamp 52 permits opening and closing of tubing 50 as desired. Air vent 48 is used to vent air which is displaced from or into volume limiting chamber 20 as parenteral solution is added to or removed from the chamber. Volume limiting chamber 20 also includes injection site 41 for injecting medication into the volume limiting chamber.

Referring now to FIG. 2, the bottom of volume limiting chamber 20 is closed by lower end cap 54 which defines outlet conduit 56 for fluidly connecting the volume limiting chamber to drip chamber 22. Lower end cap 54 also defines cylindrical sleeves 58 and 60. Cylindrical sleeve 60 defines drop-forming orifice 62 at its lower end for forming parenteral solution into drops of predetermined size. Membrane valve 64 is sealed in cylindrical rim 66 which is in turn sealed to the bottom of volume limiting chamber 20. Membrane valve 64 is sealed to mounting member 66 so that neither liquid nor air can pass between the mounting member and the membrane valve. Transparent side wall 72 of drip chamber 22 is secured to cylindrical sleeve 58 and typically comprise flexible polyvinyl chloride. Drip chamber 22 also includes lower end cap 74 which defines outlet conduit 76 for fluidly connecting drip chamber 22 to flexible tubing 26. Lower end cap 74 also defines cylindrical sleeve 78 and base portion 80.

Membrane valve 64 preferably comprises a membrane filter. In general, any membrane filter can be used which will pass parenteral solution at substantially zero pressure drop (e.g., a pressure drop of less than 10 inches of water) but when wet will not pass air under normal pressures involved in intravenous administration (i.e., a pressure corresponding to approximately 40 to 60 inches of water). These filter materials, which are well known in the art, generally have a mean pore size of less than 8 microns. A typical membrane filter is sold by Millipore Corp., Bedford, Massachusetts, as filter type SM. This membrane filter comprises mixed esters of cellulose and has a mean pore size of 5.0 microns and a bubble point of about 5 psi. The bubble point is the pressure required to force air through the pores of a water-wet filter.

Figure 5:
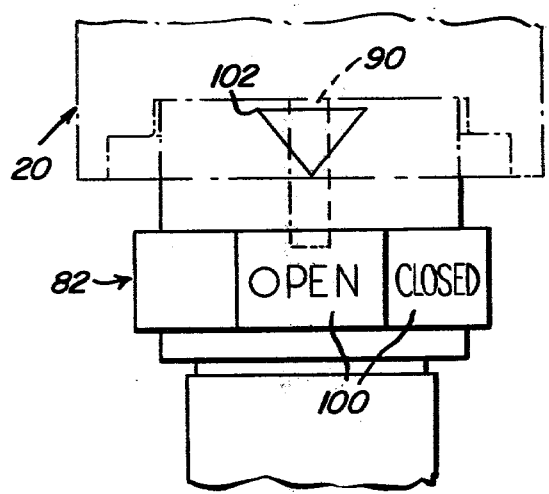
FIG. 5 is an elevational view of the drip chamber of FIG. 2.

Referring to FIGS. 2 to 5, vent cap 82 is rotatably mounted on sleeve 58 above side wall 72 of drip chamber 22. Vent cap 82 has a smooth walled bore 84 which provides an air tight fit around sleeve 58. Optionally, O ring 85 may be provided to insure an air tight fit between bore 84 and sleeve 58. When used, O ring 85 is mounted in counterbore 86 in sleeve 58. Vent cap 82 has a groove 88 on its inner surface which communicates with slot 90 extending through the vent cap wall. As seen in FIGS. 2 and 5, slot 90 provides an air path between groove 88 and the atmosphere. Air passage 92 is provided in sleeve 58 which communicates with the annulus between sleeves 58 and 60 at its unexposed end. The exposed end of air passage 92 is covered by air filter material 94 housed in counterbore 86.

Vent cap 82 is formed of a plastic such as polyethylene, polypropylene, styrene-acrylonitrile copolymer or acrylonitrile-butadiene-styrene terpolymer. Air filter material 94 comprises a semipermeable, hydrophobic membrane which is permeable to air but impermeable to parenteral solution at the pressure differentials encountered. Air filter material 94 may, for example, be formed from a thin mat of felted microscopic fibers of Teflon coated on a woven fiberglass substrate.

A boss or stop (not shown) is provided on sleeve 58 which associates with groove 96 in vent cap 82 to stop the rotation of the vent cap at the "open" and "closed" positions. If desired, lettering 100 can be provided on vent cap 82 and associated with reference mark 102 on volume limiting chamber 20 to provide a visual indication whether the valve is "open" or "closed". As will be appreciated, the valve is "open" when groove 88 is aligned with air passage 92 and "closed" when groove 88 and air passage 92 are not aligned. When the valve is "open", air can enter or leave drip chamber 22 via slot 90, groove 88, and air passage 92.

Figure 6:
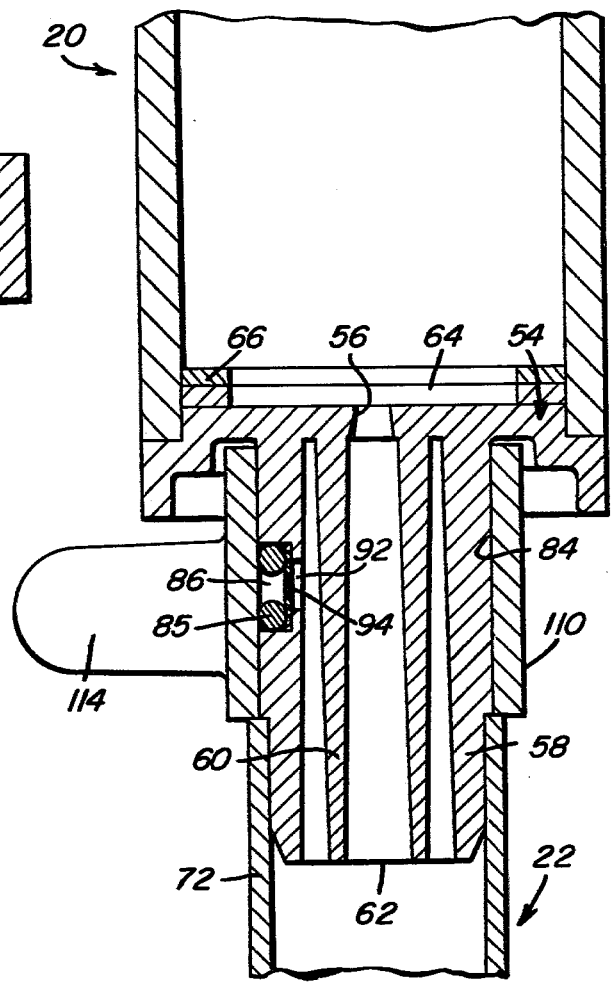
FIG. 6 is an enlarged cross-sectional view of a second embodiment of the drip chamber of this invention.

Referring now to FIG. 6, a second embodiment of this invention is shown in which vent cap 82 is replaced by a relatively wide elastomeric sealing band 110 made, for example, of latex or silicon rubber. Sealing band 110 includes band portion 112 which tightly grips the outer circumference of sleeve 58 and seals air passage 92. Sealing band 110 also includes tab 114 which is of suitable size and shape to be gripped between the thumb and forefinger. When tab 114 is pulled, air passage 92 is exposed to the atmosphere and air is admitted into the interior of drip chamber 22 or expelled therefrom.

Figure 7:
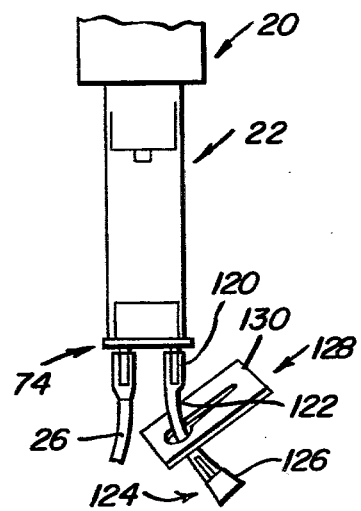
FIG. 7 is an elevational view of yet another embodiment of the drip chamber of this invention.

FIG. 7 illustrates yet another embodiment of this invention in which lower end cap 74 of drip chamber 22 has a nipple 120 which communicates with the interior of drip chamber 22. A short segment of flexible tubing 122, typically polyvinyl chloride, is connected at one end to nipple 120. The other end of tubing 122 is attached to air vent 124. Air vent 124 includes a filter cap 126 of relatively rigid plastic material over which is fitted tubing 122. Air vent 124 is of conventional construction and includes air filter material (not shown) mounted in the end of filter cap 126 which is similar to air filter material 94 used in the first and second embodiments. Flexible tubing 122 is normally closed by slide clamp 128 which basically comprises a relatively flat rigid plate 130 having a gradually tapering hole therein. When slide clamp 128 is moved to a position so that tubing 122 is no longer pinched closed, air can enter or leave drip chamber 22 via tubing 122 through a hole in the top of filter cap 126 after passing through the air filter material. It will be appreciated that this embodiment will not allow air to leave the drip chamber when tube 122 is filled with parenteral solution, as during priming.

The volume limited administration of parenteral solution using the intravenous set shown in FIG. 1 will now be described. Upper and lower compression clamps 16 and 24, respectively, are closed and piercer 12 is inserted into the outlet of a parenteral solution container which is then appropriately suspended. With slide clamp 52 open, upper compression clamp 16 is opened to allow parenteral solution to enter volume limiting chamber 20. When the desired level of parenteral solution is reached by visual reference to indicia 42, 44, upper compression clamp 16 is closed. The intravenous set is then primed by opening the air vent in drip chamber 22 by rotating vent cap 82 to the "open" position in the embodiment of FIGS. 2-5, or by pulling tab 114 on sealing band 110 in the embodiment of FIG. 6. Drip chamber 22 is then squeezed and the air vent in the drip chamber closed. Drip chamber 22 is then released and will partially fill with parenteral solution. This priming step is repeated until drip chamber 22 is about half filled.

A sterile needle is then attached to needle adapter 34. Lower compression clamp 24 is opened to allow parenteral solution to displace air in the remainder of the system and then this clamp is closed. Venipuncture is then performed and the flow rate is set by adjusting lower compression clamp 24 until the desired flow is read by reference to drip chamber 22. When the premeasured volume of parenteral solution in volume limiting chamber 20 has been delivered, the flow of parenteral solution is automatically shut off by membrane valve 64. Medication can be added by injecting through the shoulder of injection bulb 30 and/or through the rubber stopple on Y-injection site 28, or through injection site 41 in the volume limiting chamber 20. Lower compression clamp 24 is closed to prevent medication from going up flexible tubing 26 during these injection operations since this could in some instances create sufficient pressure in drip chamber 22 to rupture membrane valve 24. To refill volume limiting chamber 20, upper compression clamp 16 is opened until the desired level in the volume limiting chamber is reached. The set can also be converted from volume limited to continuous parenteral solution administration as will be readily apparent.

Referring once again to the priming operation, if drip chamber 22 is inadvertently primed to too high a liquid level, the level can be lowered simply and efficiently in accordance with the teaching of this invention. More particularly, air can be admitted into drip chamber 22 by rotating vent cap 82 to the "open" position in the embodiment of FIGS. 2-5, by pulling tab 114 on sealing band 110 in the embodiment of FIG. 6 or by adjusting slide clamp 128 in the embodiment of FIG. 7. In any of above, slide clamp 24 should be open to allow parenteral solution to flow downward in tube 26 by gravity.

While several specific embodiments of this invention have been illustrated, it should be understood that there are other embodiments falling within its scope. Accordingly, this invention should not be limited to the specific embodiments illustrated, but only as defined in the appended claims.

I claim:

1. An intravenous set comprising a volume limiting chamber for controlling the volume of parenteral solution administered to a patient and a drip chamber positioned downstream of said volume limiting chamber for determining the parenteral solution flow rate, said drip chamber comprising a transparent, flexible chamber, inlet means associated with one end of said transparent, flexible chamber for receiving a parenteral solution from said volume limiting chamber, said inlet means defining a drop-forming orifice for forming said parenteral solution into drops of a predetermined size, and outlet means associated with the other end of said transparent, flexible chamber, said outlet means adapted to discharge said parenteral solution from said transparent chamber, said volume limiting chamber having a membrane valve positioned in said volume limiting chamber so that all parenteral solution in said volume limiting chamber flows through said membrane valve, said membrane valve comprising a material which when wet will pass parenteral solution but will not pass air at normal intravenous administration pressures, and air vent means communicating directly with the interior of said drip chamber for selectively placing said drip chamber in communication with the atmosphere when said membrane valve is wet and said drip chamber is at least partially filled with parenteral solution, said air vent means comprising an air passage communicating directly with the interior of said drip chamber, said drip chamber, said membrane valve, and said air vent means each operable in a first mode for simultaneously evacuating a first volume of air from said drip chamber directly to the atmosphere without rupturing said membrane valve, and preventing parenteral solution contained in said volume limiting chamber from entering said drip chamber, each operable in a second mode for introducing a volume of parenteral solution from said volume limiting chamber into said drip chamber to substantially replace said first volume of air evacuated from said drip chamber during said first mode, and each operable in a third mode for simultaneously admitting a second volume of air directly from the atmosphere into said drip chamber, preventing parenteral solution contained in said volume limiting chamber from entering said drip chamber, and removing a volume of liquid through said outlet means, said volume of liquid being substantially equal to said second volume of air.

2. The intravenous set of claim 1 in which said air passage communicates with the interior of said drip chamber adjacent said inlet means.

3. The intravenous set of claim 1 in which said air passage communicates with the interior of said drip chamber adjacent said outlet means.

4. The intravenous set of claim 1 in which said air vent means further comprises elastomeric means for sealing said air passage.

5. The intravenous set of claim 4 and further comprising air filter means associated with the air passage to filter air flowing therethrough.

6. The intravenous set of claim 4 in which said elastomeric means comprises an elastomeric band surrounding a portion of said drip chamber and positioned to seal said air passage.

7. The intravenous set of claim 6 in which said elastomeric band has tab means for pulling said band to open said air passage.

8. The intravenous set of claim 1 in which said air vent means further comprises, flexible tubing attached at one end of said air passage, air filter means closing the other end of said flexible tubing, and clamp means associated with said flexible tubing and adapted to open and close said flexible tubing.

9. The intravenous set of claim 1 in which said air vent means further comprises rotatable valve means for opening and closing said air passage.

10. The intravenous set of claim 9 in which said air passage has air filter means associated therewith for filtering incoming air.

11. The intravenous set of claim 1 in which said volume limiting chamber includes a top and bottom and side walls connecting said top and bottom, an inlet passage in said top for placing said volume limiting chamber in fluid communication with a source of parenteral solution, an outlet passage in said bottom for placing said volume limiting chamber in fluid communication with said drip chamber, and indicia on said volume limiting chamber for indicating the amount of parenteral solution in said volume limiting chamber.

* * * * *